United States Patent [19]

Vahaviolos

[11] 3,979,670

[45] Sept. 7, 1976

[54] APPARATUS FOR DETECTING AND MEASURING PEAK-TO-PEAK VALUES IN ELECTRICAL SIGNALS

[75] Inventor: Sotirios John Vahaviolos, East Windsor Township, Mercer County, N.J.

[73] Assignee: Western Electric Company, Inc., New York, N.Y.

[22] Filed: Jan. 29, 1975

[21] Appl. No.: 545,068

Related U.S. Application Data

[62] Division of Ser. No. 389,414, Aug. 17, 1973, Pat. No. 3,924,456.

[52] U.S. Cl. .......................... 324/103 P; 307/235 A

[51] Int. Cl.$^2$ .......................................... G01R 19/16

[58] Field of Search ........... 324/103 P, 119; 321/15; 307/235 A

[56] References Cited

UNITED STATES PATENTS 2,924,769 2/1960 Harriman et al. ............... 324/103 P

*Primary Examiner*—R. V. Rolinec
*Assistant Examiner*—Ernest F. Karlsen
*Attorney, Agent, or Firm*—E. W. Pfeifle; D. J. Kirk

[57] ABSTRACT

Apparatus is disclosed for detecting and measuring peak-to-peak values in an electrical input signal, the signal comprising at least one positive-going and one negative-going peak and can include waveforms characterized by short duration and fast rise time pulses. In operation, one of the at least one input signal peaks is referenced to a predetermined d.c. voltage level, such as, for example, 0 volts d.c., and an electrical output signal is generated which is representative of the magnitude of the input signal with respect to the predetermined d.c. voltage level. The output signal is generated by electrical circuitry capable of accurately tracking fast rise time pulses and then stretching the other unreferenced at least one peaks to prevent decay thereof.

9 Claims, 8 Drawing Figures

ARTICLE
10
BASE
11
SENSOR
12
13
CHARGE AMPLIFIER
14
16
PRE-AMPLIFIER
17
18
BAND PASS FILTER
19
20
AMPLIFIER
21
GAIN SELECTOR
22
23
24
PEAK-TO PEAK DETECTOR
CLAMPING CIRCUIT
26
PEAK DETECTOR
27
28
29
COM-PARATOR
31
32
33

C
ΔC
$R_L$
e 16
43
46
54
42
-E
+E
48
41
47
51
49
44
53
52
13
12

64
61
66
-E
22
62
63
18
16
+E

83

72
76
73
77
78
71
74
-E
22
18
81
82
70
OUTPUT
+E 103
104
+E
99
23
93
94
92
INPUT
102
91
101
28
97
98
96
-E

OUT-PUT
INPUT
+E
-E

APPARATUS FOR DETECTING AND MEASURING PEAK-TO-PEAK VALUES IN ELECTRICAL SIGNALS

CROSS-REFERENCE TO RELATED APPLICATIONS

This is a division of application Ser. No. 389,414, filed Aug. 17, 1973, now U.S. Pat. No. 3,924,456, which is related to METHOD AND APPARATUS FOR DETECTING THE PRESENCE OF CRACKS IN A WORKPIECE BY THE USE OF STRESS WAVES EMITTED THEREFROM. Said copending application is assigned to the same assignee as the instant invention.

BACKGROUND OF THE INVENTION

1. Field of the Invention

The present invention relates to apparatus for detecting and measuring peak-to-peak values in electrical signals. More particularly, the present invention relates to apparatus capable of detecting and measuring peak-to-peak values in electrical signals comprising at least one positive-going and one negative-going peak.

2. Description of the Prior Art

The detection and measurement of peak-to-peak values in electrical signals has always been of interest to provide information about the signal itself, the source generating the signal, or possibly the transmission system wherein the signal propagates. The conventional implementation of a peak-to-peak detecting and measuring circuit comprises, (a) a positive peak detector and a negative peak detector for respectively measuring the magnitude of the positive peak and negative peak of an input waveform with respect to a d.c. reference voltage; and (b) a circuit to sum the magnitude of the two measured peaks to provide a peak-to-peak value. The inherent response time and signal tracking errors associated with such circuits, however, makes this type of circuitry unsuitable for use in detecting and measuring peak-to-peak values of waveforms comprising short duration and fast rise time pulses.

Waveforms comprising short duration and fast rise time pulses can, for example, be found in high frequency signals such as stress waves generated by a crack or a flaw in a brittle material which is under a load. Typical circuitry for detecting and measuring stress waves is disclosed in U.S. Pat. No. 3,713,127, issued to F. C. Keledy et al. There a peak detector and integrator circuit detects the envelope of an analog signal to charge a capacitor to a peak signal proportional to the amplitude of the envelope. This circuit, however, does not measure peak-to-peak voltages, but only indicates the magnitude of the detected acoustic energy by tracking the upper half of the envelope of the analog signal.

A subsisting problem is to provide improved method and apparatus for detecting and measuring peak-to-peak values in electrical signals comprising at least one positive-going and one negative-going peak, and especially signals also including waveforms having short duration and fast rise time pulses.

BRIEF SUMMARY OF THE INVENTION

The present invention relates to a apparatus for detecting and measuring peak-to-peak values in electrical signals and, more particularly, to apparatus for detecting and measuring peak-to-peak values in electrical signals comprising at least one positive-going and one negative-going peak, and more particularly, signals including waveforms characterized by short duration and fast rise time pulses.

The invention further relates to apparatus for detecting and measuring peak-to-peak values in an electrical signal comprising at least one positive-going and one negative-going peak wherein one of the at least one peaks is referenced to a predetermined d.c. voltage level and the magnitude of the other unreferenced at least one peaks with respect to the predetermined d.c. voltage level is indicated by a representative electrical output signal.

Other and further aspects of the present invention will become readily apparent during the course of the following description and by reference to the accompanying drawings and the appended claims.

DESCRIPTION OF THE PREFERRED EMBODIMENTS

The present invention relating to apparatus for detecting and measuring peak-to-peak values in electrical signals is herein described in relation to apparatus for detecting the presence of cracks in a workpiece by the use of stress waves emitted therefrom. However, it will be understood that such description is exemplary only and is for the purposes of exposition and not for purposes of limitation. It will be readily appreciated that the inventive concept as described is equally applicable for detecting and measuring peak-to-peak values in any electrical signal.

Figure 1:
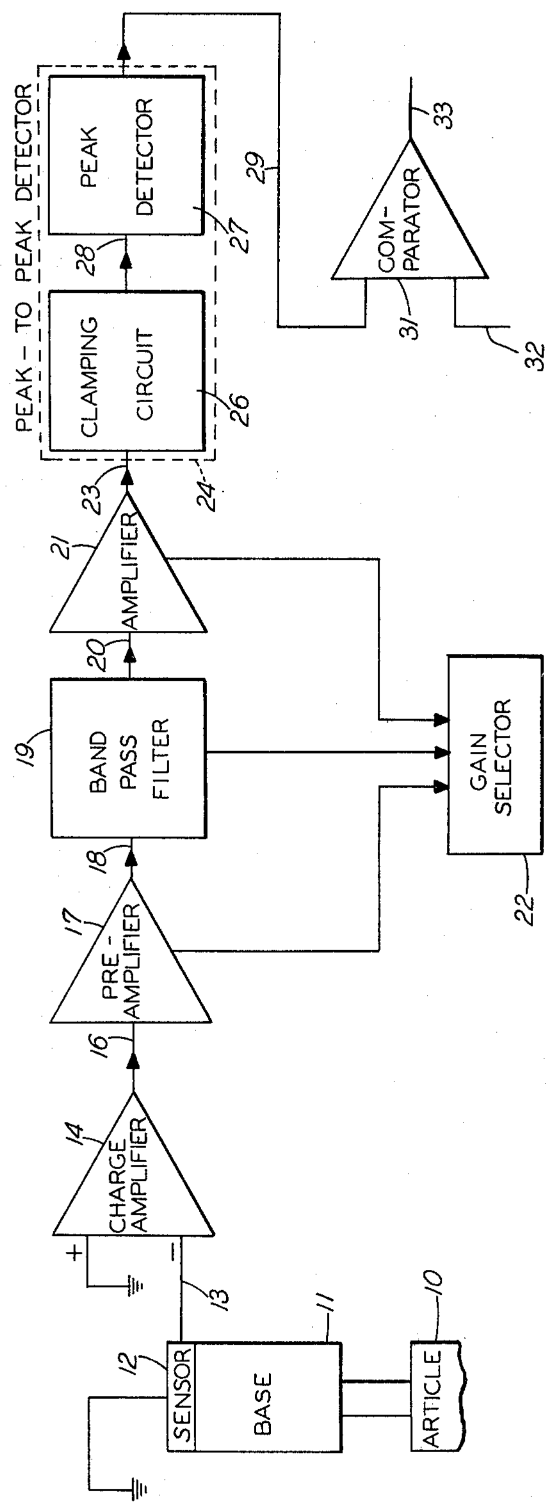
FIG. 1 is a simplified block diagram of a crack detection system according to the invention.

Referring now to FIG. 1, an article 10 to be processed is mounted on a base 11, which may be, for example, the base of a thermocompression bonder or similar device. A piezoelectric sensor 12 is mounted to the base 11. In order for sensor 12 to detect waves propagating in base 11, it is preferable that base 11 be comprised of material having a bulk sonic velocity which closely corresponds to the velocity of sound in the material of article 10. The sensor 12, of course, may also be mounted directly to article 10, but it is clearly preferable to permanently mount sensor 12 to the base 11, as shown, since less handling steps will result, resulting in faster article processing time.

The signals which are detected by sensor 12 comprise waves which are: (a) generated by other electrical components in proximity to the system of FIG. 1, but not shown; (b) generated in article 10, base 11, or sensor 12 due to nontransient factors such as temperature and strain variations; and (c) stress waves, comprising bulk and surface waves, propagating from a crack in article 10 while the article is being subjected to a load. The latter signals, when generated by a microcrack propagating in a brittle material, comprise low amplitude, short duration, and fast rise time pulses which, as previously discussed, have heretofore been hidden in system noise and, therefore, have never been detected.

Whenever crack propagation occurs, energy is released in the form of a stress wave, which wave, in turn, excites sensor 12. Depending on wave damping at the interfaces, the traveling mechanical stress impulse will cause sensor 12 to provide an output voltage change which is almost proportional to the amplitude of the impulse. Because of the low amplitude of the stress wave pulses, good transmission of the mechanical wave or amplification of the sensor's output voltage is necessary.

To obtain optimum performance from a piezoelectric sensor, the circuit to which it is connected must have certain characteristics which are dictated by the nature of the sensor. For discussion purposes, it is convenient to divide piezoelectric sensors into two broad categories, i.e., non-resonant and resonant devices. Non-resonant devices are so named because they are designed to operate well below their natural resonance and over a relatively large frequency range, usually several octaves. Resonant devices, on the other hand, are designed to operate at a single frequency, that is, the mechanical resonant frequency of the device and over a band of frequencies which is usually less than one octave, which band includes the resonant frequency of the device.

Sensors comprised of Barium Titanate and Lead Zirconate Titanate have been used in the resonance mode. Also, Lead Metaniobate sensors have been employed where relatively high sensitivity, high working temperatures, and freedom from electrical ringing are desired. All three of the above types of sensors have been employed satisfactorily in the illustrative embodiment of the invention.

Figure 2:
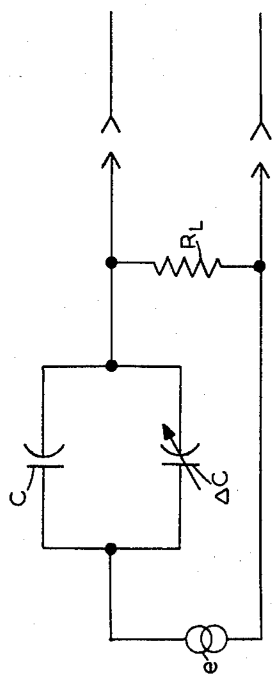
FIG. 2 is the equivalent circuit of a mechanically driven transducer of the type which may be used in the system of FIG. 1.

The equivalent circuit of a typical piezoelectric transducer is shown in FIG. 2. The change in capacitance of the equivalent sensor capacitance, $C_e'$, is the most important variable for the detection of signals. This change in capacitance, for a disc-shaped transducer, can be calculated as follows:

$$\Delta C_e' = K \left( \frac{d^2}{T} \right) \quad 1.$$

where $\Delta C_e'$ = the change of transducer's capacitance in pF;

K = the multiplier dependent on the sensitivity of the transducer;

d = the diameter of the disc in inches; and

T = the thickness of the disc in inches.

As the capacitance of the transducer varies, the charge stored thereon also varies, according to the equation $$\Delta q = - \Delta C_e' e \quad 2.$$

As shown in FIG. 1, sensor 12 is connected to the inverting input 13 of operational charge amplifier 14, said charge amplifier generating an output voltage on a lead 16 which reflects any change of charge, Δq, occurring in sensor 12. The output of amplifier 14 on lead 16 is further amplified in a low-noise preamplifier 17. Preamplifier 17, however, should advantageously be of a designn such that it has a slewing rate of at least a 100v/μ sec, since an amplifier having a lower slewing rate would substantially reduce the circuit response to pulses of short duration and fast rise time.

The output from the preamplifier 17 is transmitted over a lead 18 to a band-pass filter 19 which has a pass-band that falls at least partially within the natural frequency of sensor 12, but which falls without the range of noise frequencies generated by other components in proximity to the system.

The output of band-pass filter 19 on a lead 20 is further amplified by an amplifier 21, which also advantageously has at least a 100v/μ sec. slewing rate. A gain selector 22 permits the gain of amplifiers 17 and 21 to be adjusted, as well as any amplifiers which may be used in band-pass filter 19, as is discussed hereinafter with reference to FIG. 5. Gain selector 22 may comprise a separate potentiometer in each amplifier, but preferably comprises one potentiometer for gain adjustment of preamplifier 17 and a separate potentiometer for common gain adjustment of amplifier 21, and any amplifiers which may be used in band-pass filter 19. In the latter event, the potentiometer will proportionately change the amplification of each of the connected circuits. The gain adjustment needed is experimentally determined beforehand, the amount of gain being dependent on the nature of the article 10 being processed, and the reflection and attenuation of the stress waves emitted from article 10. It has been found that as the material in article 10 becomes more brittle, less amplifier gain is needed to detect and measure the stress waves emitted therefrom.

The amplified and filtered output from amplifier 21 on a lead 23 is transmitted to a peak-to-peak detector and measuring circuit 24 which is capable of measuring short duration, fast rise time pulses. In the preferred embodiment of the invention, a novel peak-to-peak detector 24, comprising a precision clamping circuit 26 and a peak detector 27, as discussed hereinafter with reference to FIGS. 6 and 7 respectively, is employed. As will be more fully explained herebelow, the clamping circuit 26 references the input signal on lead 23 to a predetermined d.c. voltage level, preferably 0 volts d.c. The referenced signal is transmitted on a lead 28 to peak detector 27 where the magnitude of the signal is determined with respect to the predetermined d.c. voltage level. An indication of the determined magnitude is transmitted over a lead 29 to a comparator circuit 31 which compares the magnitude of the signal on lead 29 with a signal which is proportional to the system noise level, as present on a lead 32. When the magnitude of the referenced signal on lead 29 exceeds the system noise level, an output signal indicating a detected crack is provided on lead 33 to some suitable audio or video indicating device, not shown.

Figure 3:
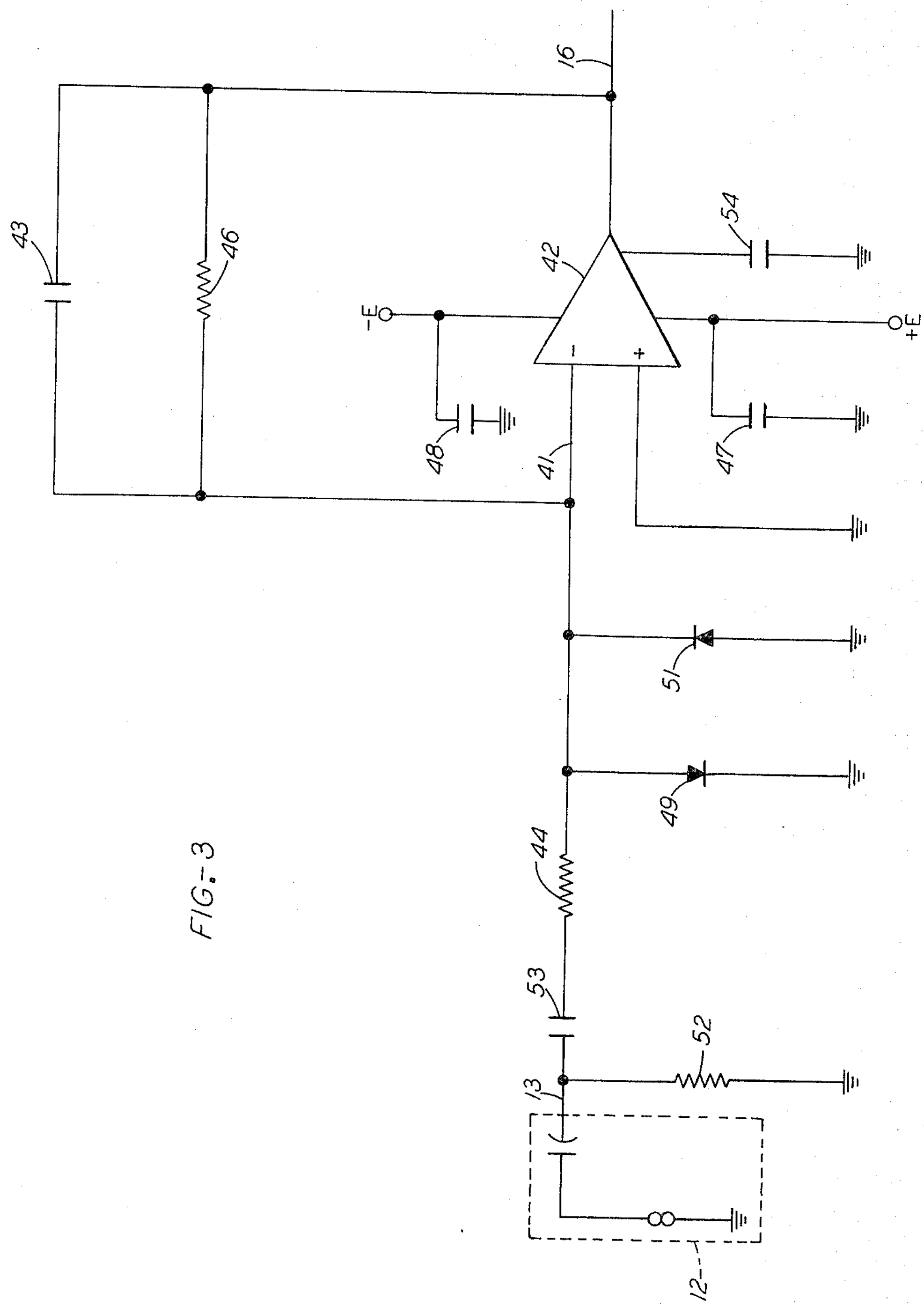
FIG. 3 is the circuit diagram of a novel charge amplifier which may advantageously be used in the system of FIG. 1.

Referring now to FIG. 3, the effect of the sensor's high output impedance is overcome by using an FET operational amplifier 42 having an extremely high input impedance, low bias current, and wide bandwidth. When sensor 12 is connected to the inverting input 41 of operational amplifier 42, as shown in FIG. 3, the incremental charge given by equation 2, above, flows into a feedback capacitor 43. The resultant change in charge on capacitor 43 generates an amplifier output voltage Vo given by the equation $$V_o = -\frac{\Delta C_s'}{C_f} e \qquad 3.$$

where $C_f$ = the value of the feedback capacitor.

The frequency response of charge amplifier 42 advantageously extends from 1Hz to 10MHz (±3dB). A resistor 44, which is connected in series between sensor 12 and inverting input 41, isolates the capacitive source from the feedback loop in the megahertz region and helps to reduce overshoot or noise. At low frequencies the response of amplifier 42 is −3dB at the frequency at which the reactance of capacitor 43 is equal to the resistance of a feedback resistor 46. The maximum permissible value of resistor 46 is determined by the allowable output offset and the input current of the amplifier at the highest operating temperature.

Because of the very low input current to the FET-input amplifier 42, a very high value of feedback resistance 46 can be used to supply the d.c. bias current, which results in a low noise level of about 100μV RMS over a 10Hz to 1MHz bandwidth, when the amplifier is connected to a 2000pF source capacitor.

As shown in FIG. 3, a pair of capacitors 47 and 48 are connected to amplifier 42 and are connected in series across a source of power for the amplifier. A pair of diodes 49 and 51, connected in parallel but oppositely poled, are connected between the inverting input 41 of amplifier 42 and ground, to protect amplifier 42 from any high-voltage surges which may occur in sensor 12 due to abrupt temperature or strain variations. A resistor 52, connected between input-lead 13 and ground, and a capacitor 53, connected between sensor 12 and input resistor 44, form a bleed network, heretofore never used in prior art charge amplifiers, for passing only transient waveforms from sensor 12 to amplifier 42. The bleed network, therefore, prevents steady state voltages, e.g., resulting from heating and expansion of sensor 12, from affecting the operation of the charge amplifier 42 operation. A capacitor 54, connected between amplifier 42 and ground, provides a known form of bandwidth control.

The output of charge amplifier 14 is further amplified in a low-noise preamplifier 17.

Although operational amplifiers are generally designed to amplify d.c. signals, they have rather broad frequency response and are consequently quite useful for strictly a.c. signals. The feedback network used with an operational amplifier can be tailored for exactly the desired pass-band by various known methods of RC compensation.

Figure 4:
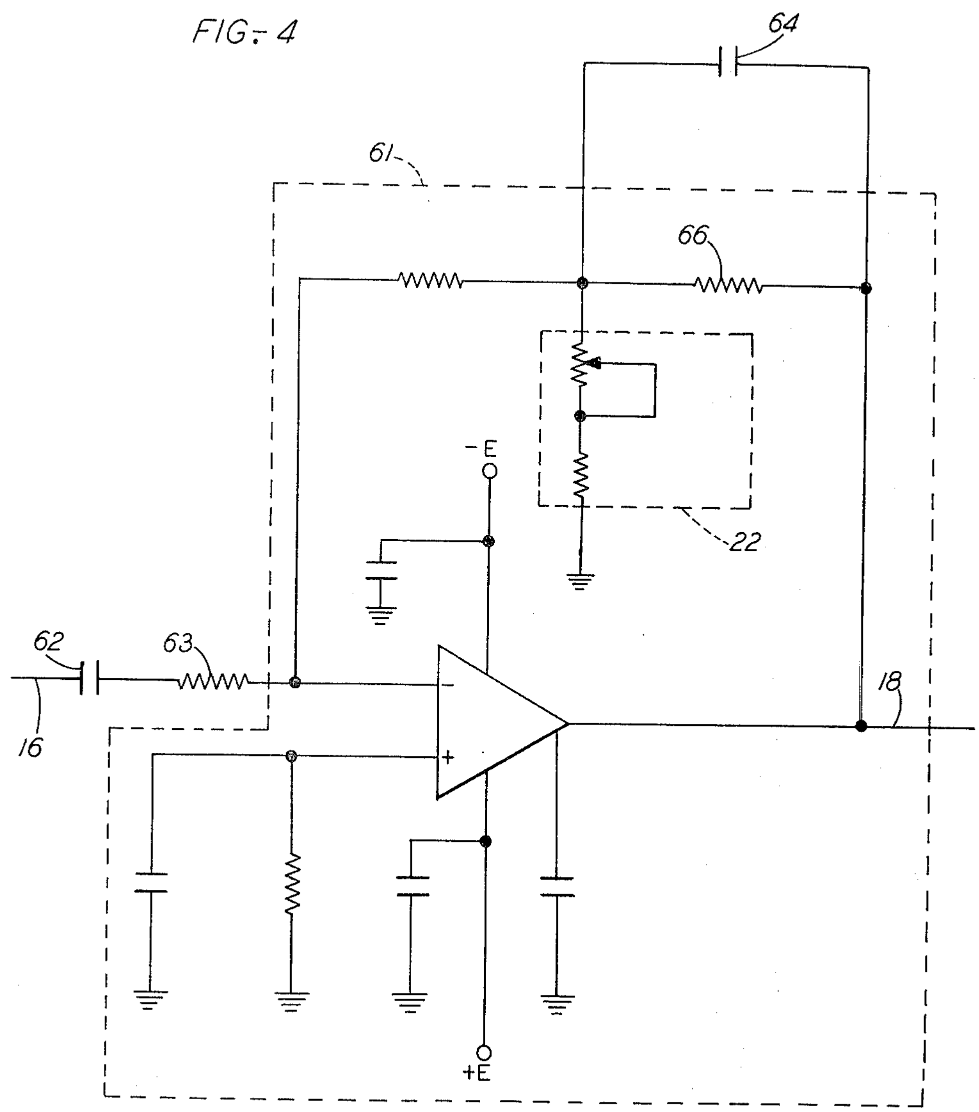
FIG. 4 is a circuit diagram of a low-noise amplifier for use with the system of FIG. 1.

A very simple and stable prior art amplifier configuration 61 is shown in FIG. 4. The prior art amplifier has been modified, according to the invention by the addition of a capacitor 62 and a resistor 63 is series with the input lead 16 to limit the low frequency bandwidth and thereby reduce noise. Capacitor 62 blocks the d.c. component of the input signal and, together with the resistor 63, sets the low frequency 3dB response point for the overall amplifier. Amplifier 61 has been further modified to reduce noise by connecting a capacitor 64 across a feedback resistor 66, capacitor 64 thereby limiting the high frequency bandwidth of amplifier 61. The preamplifier's gain should be variable, as mentioned previously, since the capacitance C of the equivalent circuit of sensor 12 used in equation 1 is only an approximation.

With reference to the filter 19 shown in FIG. 1, the desired band-pass characteristic can be achieved by using a low-pass and high-pass Butterworth filter section in cascade. However, the preferred circuit employs the novel active filter stage 71 shown in FIG. 5. This filter stage comprises an operational amplifier 70 which includes a Twin-T network, comprising resistors 72, 73 and 74 and capacitors 76, 77 and 78, in the feedback loop. Filter stage 71 not only provides the desired pass-band but also provides additional amplification of the signals passing therethrough. The pass-band of the filter stage is determined by the values of resistors 72–74 and capacitors 76–78 in accordance with well-known principles. Since the pass-band is changed when the values of resistors 72–74 are simultaneously varied, it is convenient to use resistors which are ganged on a single shaft for adjusting the filter stage 71 to a desired pass-band.

Figure 5:
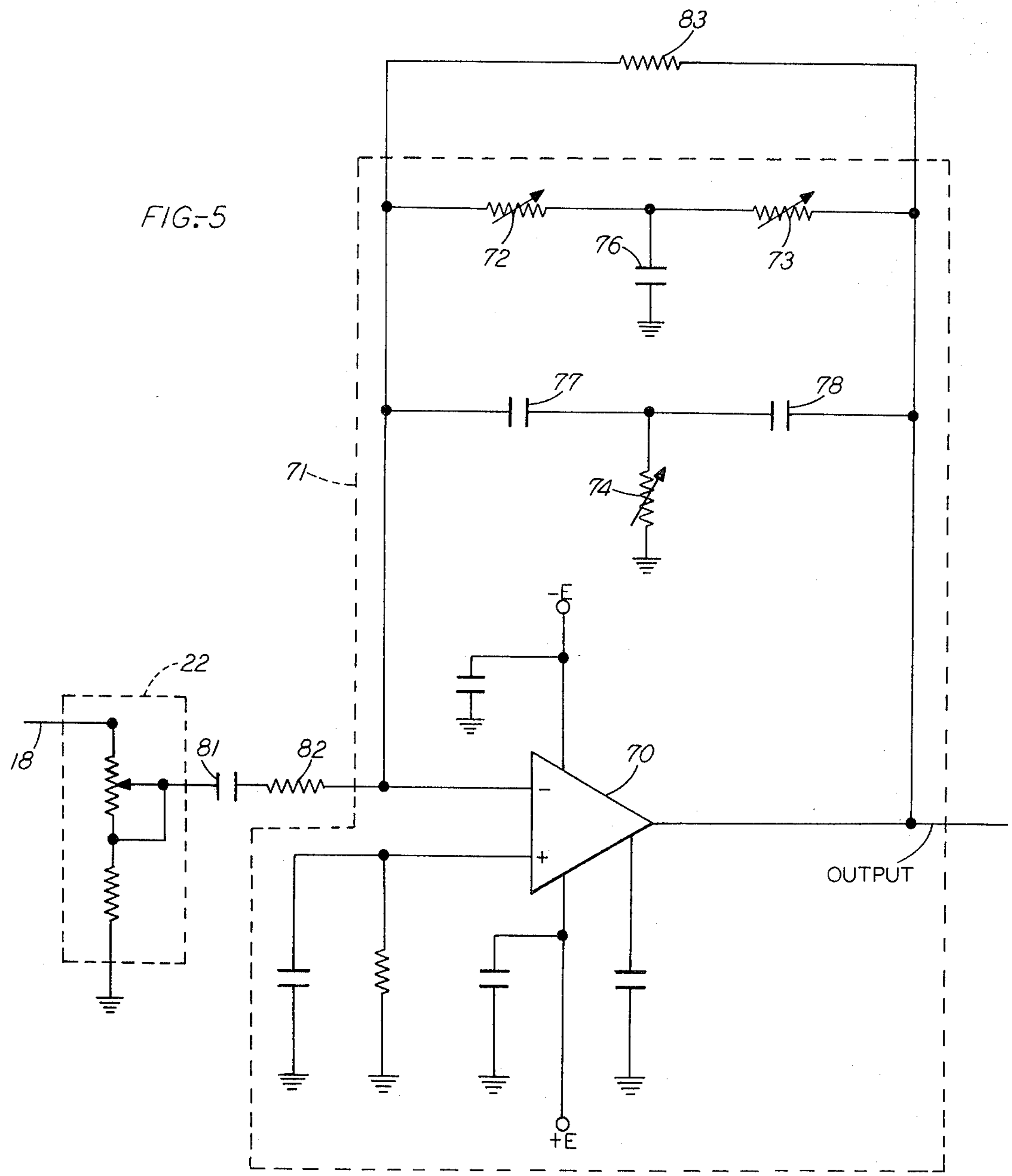
FIG. 5 is the circuit diagram of a Twin-T filter stage which may advantageously be used in the system of FIG. 1.

The Twin-T feedback network, however, causes a large amount of "ripple" over the wide frequency spectrum, e.g., from 0.3MHz to 1.2MHz, which is passed by the notch filter of FIG. 5. A capacitor 81 and a resistor 82, connected in series with the input lead 18 to filter stage 71, smoothes the ripple in the filter which is caused by the feedback network. A resistor 83 is connected across the feedback network to limit the depth of the notch provided by filter stage 71, thus providing a better signal-to-noise ratio.

Although only one stage is shown for band-pass filter 19, a plurality of similar stages can be serially connected, as desired, each stage providing an additional 2nd. order wave to further sharpen the notch response. In the preferred embodiment of the invention, three such stages are serially connected to provide a 6th. order band-pass filter.

The conventional implementation of a peak-to-peak detector comprises: (a) a positive peak detector and a negative peak detector for respectively measuring the magnitude of the positive peak and the negative peak of an input waveform, with respect to a d.c. reference voltage; and (b) a circuit to sum the values so produced to arrive at an indication of the overall magnitude of the input waveform. The problems associated with prior art designs of this type are response time and large signal tracking errors. By utilizing the novel peak-to-peak detector and measuring circuit shown in FIGS. 6 and 7, the response time is improved, since fewer components are used. Further, the use of only one peak detector keeps input signal tracking errors at a minimum.

A function that must frequently be accomplished with a periodic waveform is the establishment of the recurrent positive or negative extremity at some constant reference level $V_R$. Since, in the steady state, circuits used to perform this function restrain the extremity of the waveform from going beyond the reference level $V_R$, the circuit is usually referred to as a "clamping circuit." Generally, whenever a circuit point becomes connected through a low impedance (for example, a conducting precision diode) to some reference voltage $V_R$, then that point has been clamped to $V_R$, since the voltage will not be able to depart appreciably from $V_R$. The novel precision clamping circuit of FIG. 6 uses a conventional operational amplifier 91, altered as hereinafter described.

The output of amplifier 21 in FIG. 1 is connected to clamping circuit 26 over lead 23, more particularly to the inverting input of operational amplifier 91. Connected serially in input lead 23 is a capacitor 93 and a resistor 94 which form a clamping network that shifts the incoming wave to the reference level. A resistor 96 is connected between lead 23 and ground, ahead of the clamping network, to reflect any noise components back into the output of amplifier 21. A diode 97 and a pair of diodes 98 and 99, respectively connected to the input and output of amplifier 91, provide amplifier protection to prevent saturation or latching.

The novel means whereby the bandwidth of the amplifier 91 is extended comprises a serially connected capacitor 101 and a resistor 102, connected across the inverting and non-inverting inputs of amplifier 91. The novel means for substantially reducing "overshoot" in the clamping circuit 22 comprises connecting a parallel-connected capacitor 103 and a resistor 104 in the feedback path of amplifier 91.

Figure 7:
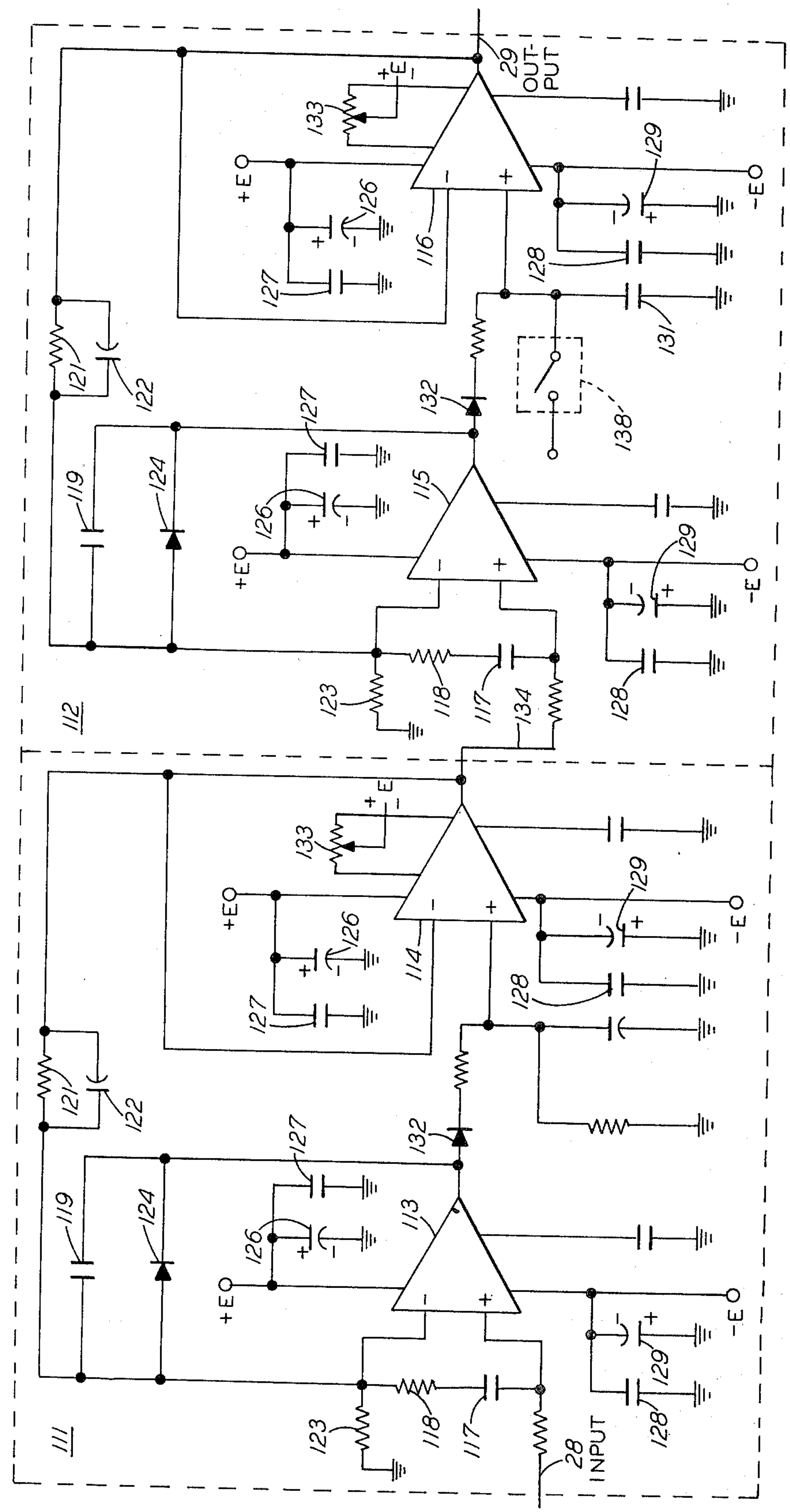
FIG. 7 is a circuit diagram of a peak detector and a peak-stretch circuit for use in the novel peak-to-peak detector of FIG. 6.

Referring to FIG. 7, the schematic circuit of a novel peak detector and measuring circuit according to the invention is shown. This detector and measuring circuit is advantageously used for peak detector 27 in FIG. 1. The detector includes a peak detecting section 111 which, in combination with a peak stretching section 112, responds to input pulses greater than 1MHz while nevertheless maintaining a low droop rate. High speeds are achieved by the use of a plurality of high slew-rate operational amplifiers 113–114 and 115–116 serially connected to each other in sections 111 and 112, respectively.

Figure 6:
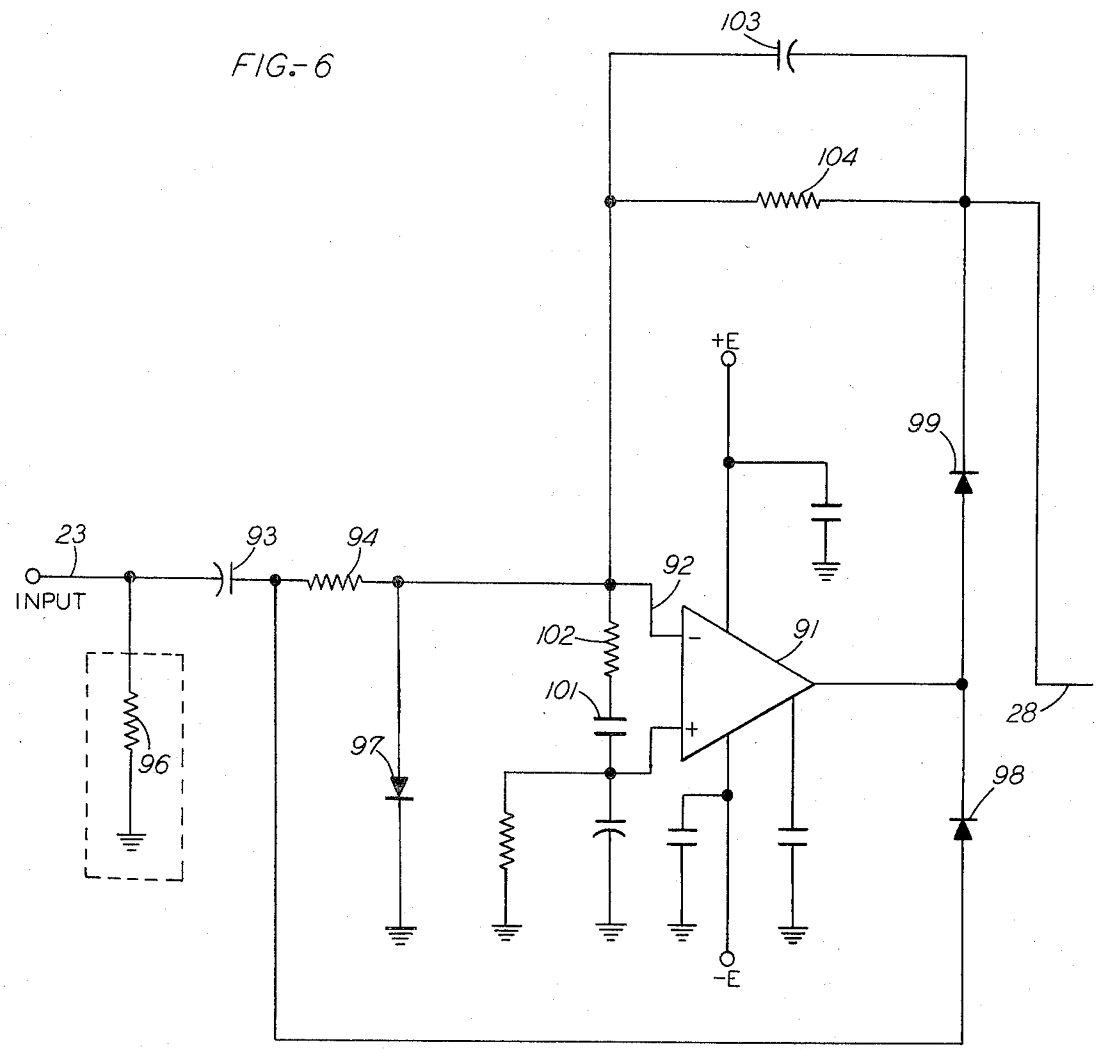
FIG. 6 is the circuit diagram of a clamping circuit for use in a novel peak-to-peak detector.

The output of clamping circuit 26 shown in block diagram form in FIG. 1 and schematically in FIG. 6 is connected to the non-inverting input of amplifier 113 over lead 28. The output of amplifiers 113, 114 and 115 are respectively connected to the non-inverting inputs of amplifiers 114, 115 and 116. A network comprising a capacitor 117 serially connected with a resistor 118 is connected across the inverting and non-inverting inputs of amplifiers 113 and 115 to extend the bandwidth of sections 111 and 112, respectively.

The final amplifiers 114 and 116 in sections 111 and 112, respectively, each include a feedback network comprising a capacitor 119 connected in series with the parallel combination of a resistor 121 and a capacitor 122. A resistor 123 is connected between each of the inverting inputs of amplifiers 113 and 115 and ground. The resistors 121 and 123, in each of the sections 111 and 112, in conjunction with capacitors 119 and 122, provide gain control for minimal "overshoot" characteristics, the latter capacitors helping to reduce overshoot and uncertainty since a constant level of minimal overshoot always remains and is determinable.

A diode 124 is connected across the inverting input and the output of amplifiers 113 and 115 and a diode 132 is connected between amplifiers 113–114 and 115–116, to provide protection for the amplifiers. To reduce noise, power supply coupling capacitors 126–129 are connected in parallel between the power supply terminals and ground in each of amplifiers 113–116. As mentioned previously, section 111 detects the peak of the input wave on lead 28 and section 112 stretches the wave peaks, effectively preventing discharge of a capacitor by expanding the peaks. A capacitor 131 connected between the non-inverting input of amplifier 116 and ground provides the peak stretching capability of section 112.

Figure 8:
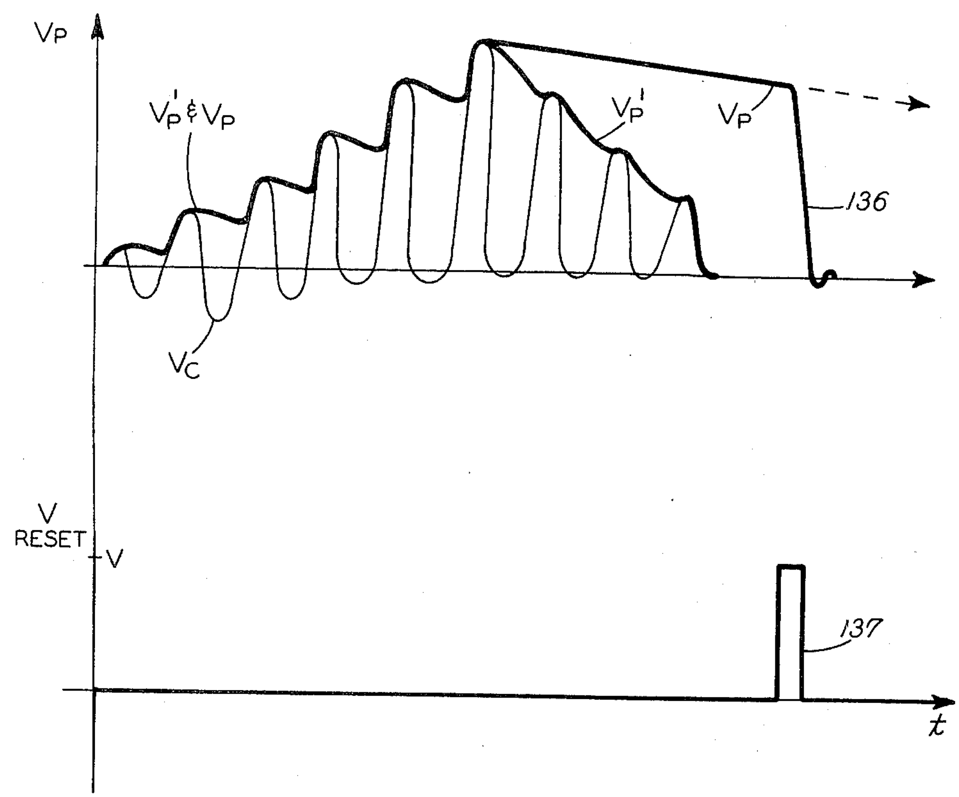
FIG. 8 depicts the input and output waveforms of both the clamping circuit and the peak detector shown in FIGS. 6 and 7, respectively.

Referring to FIG. 8, a typical set of waveforms is shown to aid in understanding the function of sections 111 and 112 of FIG. 7. Waveform Vc represents an input wave to peak detection section 111 from clamping circuit 26 via lead 28. Waveform V'p represents the output wave from peak detection section 111, as found on lead 134 of FIG. 7, which wave also represents the input to pulse stretching section 112. Waveform Vp represents the output of pulse stretching section 112 on lead 29 and depicts the stretching of the V'p pulses as the peaks of waveform Vc first increase and then decrease in value. The sharp decrease 136 of waveform Vp results from a reset pulse 137, produced by a commercially available solid state switch 138 and its associated circuitry (not shown), which reset pulse is introduced into pulse stretching section 112 once the maximum peak has been measured.

The preferred embodiment of the present invention, as described above, is capable of operating at a signal-to-noise ratio of at least 200:1. As shown in FIG. 1, a decision comparator 31 is inserted into the system to receive the output signal of peak-to-peak detector and measuring circuit 24 in order to decide if the signal generated therein exceeds an empirically preset noise threshold. The threshold to be used is a function of the electrical noise generated by the apparatus on which the present system is used, and by the large spikes typically carried by the a.c. line in a factory environment. Thresholds of 1.0 volts can be a typical value but the value is mainly determined from the surrounding conditions of the system.

Decision making comparators can also be used to further analyze the degree of crack damage. That is, in processing electronic substrates, "corner chip-offs" or glass substrate "flop-offs" can be detected and distinguished from "complete substrate cracks."

There exists a relationship between the amount of crack propagation and the output voltage of the present system. Two comparators can thus be used, one corresponding to "corner chip-offs," possible with a system threshold voltage of between 1.5V and 2.5V, and one for "complete cracks" with a system threshold voltage possibly above 2.5V. This approach may be used as a screening and grouping procedure for further processing. The information generated from a particular comparator can be audibly or visually displayed, by means of any suitable indication circuit.

The system, according to the invention, uses economically produced, low-noise, reliable wideband circuits which, when interconnected with a 3-stage Twin-T active filter, as described above, enables the detection of signals in a narrow 100KHz frequency range located, for example, between 0.3KHz and 1MHz. The frequency range chosen depends on the material being tested and on the signals generated by external components in proximity to the system. The present invention is also capable of detecting high frequency stress waves emitted through irregular surfaces connected only with integrated circuit pin supports. With an open output and the sensor connected to the input the present system produces noise values equal to only approximately 1/2mv, when using a minimal overall gain of approximately 150, and approximately 20mv when using a maximum overall gain of approximately 15,000.

The present invention can be used not only to detect non-visual cracks as they are propagated, but in so doing eliminates the need for visual inspection of finished products for cracks. The system can be a very useful tool not only in the detection of cracks but also in the identification of problem areas causing cracks. As an example, if the present crack detector is used on a bonder and detects small cracks or "corner chip-offs," then it is time for calibration of the bonder since further degradation will cause substrate "complete cracks" (useless product). A crack in either one of two materials being bonded together may also be detected.

It is to be understood that the above-described arrangement of components, circuits and cooperation of elements are simply illustrative of the principles of the invention and many other modifications may be made without departing from the spirit and scope of the invention.

What I claim is:

1. Apparatus for detecting and measuring peak-to-peak values in an electrical input signal comprising a group of positive-going peaks and a group of negative-going peaks, the apparatus comprising:

a clamping circuit for referencing one of said group of peaks to a predetermined d.c. voltage level, comprising:

an operational amplifier having an inverting input for receiving the input signal, a non-inverting input, and an output terminal; and a first network, connected to said inverting input, to reference one of the groups of peaks of the input signal to said predetermined d.c. voltage; and a peak detecting and measuring circuit connected to said clamping circuit for providing an electrical output signal indicative of the magnitude of the other unreferenced peaks with respect to said predetermined d.c. voltage level.

2. Apparatus according to claim 1, wherein the clamping circuit further comprises:

a second network, connected between said inverting and said non-inverting inputs to extend the bandwidth of said clamping circuit.

3. Apparatus according to claim 2, wherein the clamping circuit further comprises a third network, in the feedback loop, for substantially reducing overshoot in said clamping circuit.

4. Apparatus according to claim 2, wherein the clamping circuit further comprises a fourth network connected to the inverting input of said operational amplifier to reflect any noise components present in said input signal back toward the source thereof.

5. Apparatus according to claim 1, wherein said predetermined d.c. voltage is 0 volts d.c.

6. Apparatus for detecting and measuring peak-to-peak values in an electrical input signal comprising a group of positive-going peaks and a group of negative-going peaks, the apparatus comprising:

means for referencing one of said group of peaks to a predetermined d.c. voltage level;

a peak detecting and measuring circuit connected to said referencing means for providing an electrical output signal indicative of the magnitude of the other unreferenced peaks with respect to said predetermined d.c. voltage level, the peak detecting and measuring circuit further comprises:

a peak detecting section having an operational amplifier with an inverting and a non-inverting input and a network connected between said inverting and said non-inverting inputs to extend the bandwidth of said peak detecting section; and a pulse stretching section receiving the output wave from said peak detection section to maintain the level of each detected other unreferenced group of peaks with minimal decay and generate said electrical output signal.

7. Apparatus according to claim 6, wherein said pulse stretching section comprises at least one pulse stretching stage including:

an operational amplifier having an inverting and a non-inverting input, and a network connected between said inverting and said non-inverting inputs to extend the bandwidth of said pulse stretching section.

8. A peak detector according to claim 6, wherein said peak detecting section further comprises means for providing a substantially constant level of minimal overshoot in the tracking of said clamped input signal from said clamping means.

9. Apparatus according to claim 7, wherein said pulse stretching section further comprises means for providing a substantially constant level of minimal overshoot in the tracking of said clamped input signal from said clamping means.

* * * * *

UNITED STATES PATENT OFFICE
CERTIFICATE OF CORRECTION

Patent No. 3,979,670 Dated September 7, 1976

Inventor(s) S. J. VAHAVIOLOS

It is certified that error appears in the above-identified patent and that said Letters Patent are hereby corrected as shown below:

Column 4, line 8, "designn" should read --design--. Column 5, equation (3), that portion of the equation reading "$V_o =$ " should read --$V_o \simeq$ --. Column 7, line 20, "circuit 22" should read --circuit 26--.

Column 9, lines 25 and 28, the paragraphs should be indented twice.

Signed and Sealed this

Fourth Day of January 1977

[SEAL]

*Attest:*

RUTH C. MASON
*Attesting Officer*

C. MARSHALL DANN
*Commissioner of Patents and Trademarks*